(12) United States Patent
Holman et al.

(10) Patent No.: US 7,708,928 B2
(45) Date of Patent: May 4, 2010

(54) PROCESS FOR FORMING MEDICAL DEVICE BALLOONS

(75) Inventors: Thomas Holman, Minneapolis, MN (US); Nam H. Hoang, Minneapolis, MN (US); Jeffrey S. Lindquist, Maple Grove, MN (US); Richard Dunn, Brooklyn Park, MN (US); Scott Schewe, Eden Prairie, MN (US); Kevin Silberg, Big Lake, MN (US); David Parsons, Princeton, MN (US); Ken Xiao Kang Zhang, Maple Grove, MN (US); Afsar Ali, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 12/336,073

(22) Filed: Dec. 16, 2008

(65) Prior Publication Data

US 2009/0096134 A1  Apr. 16, 2009

Related U.S. Application Data

(60) Division of application No. 11/849,913, filed on Sep. 4, 2007, now Pat. No. 7,465,164, which is a continuation of application No. 10/753,043, filed on Jan. 7, 2004, now Pat. No. 7,264,458.

(51) Int. Cl.
*B29C 49/64* (2006.01)

(52) U.S. Cl. .......... 264/454; 264/458; 264/482; 264/521

(58) Field of Classification Search ............ 264/454, 264/458, 482, 492, 521
See application file for complete search history.

(56) References Cited

U.S. PATENT DOCUMENTS

| 4,233,022 | A | 11/1980 | Brady et al. |
| 4,490,421 | A | 12/1984 | Levy |

(Continued)

FOREIGN PATENT DOCUMENTS

EP      0540858      5/1993

(Continued)

OTHER PUBLICATIONS

U.S. Appl. No. 10/617,428, filed Jul. 7, 2003, Schewe et al.

*Primary Examiner*—Robert B Davis
(74) *Attorney, Agent, or Firm*—Vidas, Arrett & Steinkraus (57) ABSTRACT

Medical device balloons are formed from a tubular parison by a process or apparatus which establishes a controlled location (initiation zone) on the parison where radial expansion is initiated. Initiation within the initiation zone is achieved by heating the parison in that location to a higher temperature than the remainder of the parison for at least a portion of the blowing time. A variety of apparatus configurations are provided, some of which allow for the size and location of the initiation zone to be readily reconfigured. Balloons can also be modified, post-blowing, using heating apparatus and methods described.

23 Claims, 3 Drawing Sheets

U.S. PATENT DOCUMENTS

| | | |
|---|---|---|
| 4,906,244 A | 3/1990 | Pinchuk et al. |
| 4,935,190 A | 6/1990 | Tennerstedt |
| 4,950,239 A | 8/1990 | Gahara et al. |
| 4,963,313 A | 10/1990 | Noddin et al. |
| 5,017,325 A | 5/1991 | Jackowski et al. |
| 5,087,394 A | 2/1992 | Keith |
| 5,087,520 A | 2/1992 | Suzuki et al. |
| 5,096,848 A | 3/1992 | Kawamura |
| 5,250,069 A | 10/1993 | Nobuyoshi et al. |
| 5,254,091 A | 10/1993 | Aliahmad et al. |
| 5,264,260 A | 11/1993 | Saab |
| 5,270,086 A | 12/1993 | Hamlin |
| 5,290,306 A * | 3/1994 | Trotta et al. ................. 606/194 |
| 5,304,340 A | 4/1994 | Downey |
| 5,306,246 A | 4/1994 | Sahatjian et al. |
| 5,328,468 A | 7/1994 | Kaneko et al. |
| 5,330,428 A | 7/1994 | Wang et al. |
| 5,334,146 A | 8/1994 | Ozasa |
| 5,344,400 A | 9/1994 | Kaneko et al. |
| 5,403,340 A | 4/1995 | Wang et al. |
| 5,411,477 A * | 5/1995 | Saab .................... 604/103.13 |
| 5,500,180 A | 3/1996 | Anderson et al. |
| 5,556,383 A | 9/1996 | Wang et al. |
| 5,614,136 A | 3/1997 | Pepin et al. |
| 5,645,789 A | 7/1997 | Roucher, Jr. |
| 5,714,110 A | 2/1998 | Wang et al. |
| 5,792,415 A | 8/1998 | Hijlkema |
| 5,797,877 A | 8/1998 | Hamilton et al. |
| 5,826,588 A | 10/1998 | Forman |
| 5,833,657 A | 11/1998 | Reinhardt et al. |
| 5,853,389 A | 12/1998 | Hijlkema |
| 5,869,110 A | 2/1999 | Ogihara |
| 5,891,386 A | 4/1999 | Deitermann et al. |
| 5,951,513 A | 9/1999 | Miraki |
| 6,004,289 A | 12/1999 | Saab |
| 6,024,752 A | 2/2000 | Horn et al. |
| 6,146,356 A | 11/2000 | Wang et al. |
| 6,193,738 B1 | 2/2001 | Tomaschko et al. |
| 6,270,522 B1 | 8/2001 | Simhambhatla et al. |
| 6,287,506 B1 | 9/2001 | Hudgins et al. |
| 6,290,485 B1 | 9/2001 | Wang |
| 6,328,710 B1 | 12/2001 | Wang et al. |
| 6,358,227 B1 | 3/2002 | Ferrera et al. |
| 6,436,056 B1 | 8/2002 | Wang et al. |
| 6,465,067 B1 | 10/2002 | Wang et al. |
| 6,495,090 B1 | 12/2002 | Wilkins |
| 6,572,813 B1 | 6/2003 | Zhang et al. |
| 6,875,197 B1 | 4/2005 | Simhambhatla et al. |
| 6,905,743 B1 | 6/2005 | Chen et al. |
| 6,979,420 B2 | 12/2005 | Weber |
| 7,435,077 B2 * | 10/2008 | Schewe et al. .............. 425/526 |
| 2002/0041940 A1 | 4/2002 | Jung, Jr. et al. |
| 2002/0103455 A1 | 8/2002 | Zhang et al. |
| 2002/0110657 A1 | 8/2002 | Wang et al. |
| 2002/0171180 A1 | 11/2002 | Simhambhatla |
| 2003/0167067 A1 | 9/2003 | Wang et al. |
| 2003/0183967 A1 | 10/2003 | Weber |
| 2005/0008806 A1 | 1/2005 | Schewe et al. |
| 2005/0228428 A1 | 10/2005 | Ali et al. |

FOREIGN PATENT DOCUMENTS

| | | |
|---|---|---|
| WO | 98/32118 | 7/1998 |
| WO | 00/01420 | 1/2000 |
| WO | 01/51115 | 7/2001 |

* cited by examiner

PROCESS FOR FORMING MEDICAL DEVICE BALLOONS

CROSS-REFERENCE TO RELATED APPLICATIONS

This application is a Division of application Ser. No. 11/849,913, filed Sep. 4, 2007, pending, which is a Continuation of application Ser. No. 10/753,043, filed Jan. 7, 2004, now U.S. Pat. No. 7,264,458, the contents of both of which are hereby incorporated by reference in their entirety.

FIELD OF THE INVENTION

The present invention relates to a process for making balloons for catheters used in medical dilatation procedures, and to improved apparatus therefor.

BACKGROUND OF THE INVENTION

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices vary according to the specific application, but for many applications a high strength robust balloon is necessary and good softness and trackability properties are highly desirable.

Commercial high strength balloons having wall strengths in excess of 20,000 psi, have been formed of a wide variety of polymeric materials, including PET, nylons, polyurethanes and various block copolymer thermoplastic elastomers. U.S. Pat. No. 4,490,421, Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al, and U.S. Pat. No. 6,146,356, Wang et al, describe balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. U.S. Pat. No. 5,833,657, Reinhart et al, describes balloons having a layer of polyetheretherketone. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons.

A variety of blow forming techniques have been utilized. The extruded parison may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents already mentioned or in U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al, U.S. Pat. No. 5,304,340, Downey.

Following blow-forming the balloons may be simply cooled, heat set at a still higher pressure and/or temperature or heat shrunk at an intermediate pressure and/or temperature, relative to the blow forming temperature and pressure. See U.S. Pat. No. 5,403,340, Wang et al. EP 540858, Advanced Cardiovascular Systems, Inc.; and WO 98/03218, Scimed Life Systems.

In commonly owned copending US application published as US 2003-0167067 A1, Wang et al., incorporated herein by reference, it is disclosed that improved balloon properties can be obtained by controlling the parison extrusion in a manner which restricts the elongation of the parison material in the longitudinal direction.

U.S. Pat. No. 5,714,110, Wang et al., describes a method for forming a catheter balloon comprising the steps of placing tubing of a thermoplastic material in a mold and blowing the balloon by pressurizing and tensioning the tubing while gradually dipping the mold into a heated heat transfer media so as to sequentially blow the first waist, the body and the second waist portions of the balloon, the tubing being subjected to a relatively lower pressure while the body portion is blown than while the first and second waist portions are blown.

In commonly owned copending U.S. application Ser. No. 10/617,428, filed Jul. 7, 2003, Schewe, et al, entitled "Medical Device Tubing With Discrete Orientation Regions", methods of forming extruded tubular polymeric segments with a varied orientation or elongation along the length thereof are disclosed.

In U.S. Pat. No. 6,572,813, Zhang et al, an apparatus is described in which a mold form is heated by mechanically moving one or more external heaters along the outside of a balloon mold containing a tubular parison. The document states that the temperature of the parison, along the effective length of the mold should be kept within a specified minimum difference, for instance 100° C. and preferably within 20° C. That is, a relatively non-uniform heating apparatus is controlled to provide a more uniform heating. In this respect the system is understood to merely mimic heating behaviour of well known balloon molding systems, for instance those in which mold forms are dipped into a heated liquid bath and those in which a block heater surroundingly contacts the mold.

In mass production of medical device balloons, some processes produce substantial rejection rates. Parison shaping techniques going beyond simple axial stretching and radial expansion of straight tubes tend to increase balloon rejection rates. Grinding or necking down ends of a parison may have such an effect. Nevertheless, shaped parisons are often needed, for instance to allow large diameter balloons to be fashioned with high burst strength and/or for mounting on small diameter catheters. A free-blowing step in a balloon forming process can also display such problems.

Process improvements in the balloon forming art which minimize rejection rates are desirable both for the direct reduction in manufacturing cost and for the reduced likelihood that a defective balloon will escape inspection. Consequently there is ongoing need for process improvements in the medical balloon forming arts.

SUMMARY OF THE INVENTION

The invention relates to a method of making a balloon and apparatus for carrying out the same The present inventors have concluded that an important factor accounting for a substantial number of balloon rejects is the location on the parison that radial expansion is initiated in the balloon forming process. Current, conventional, balloon-molding process technology do not allow for repeatable, accurate control of molding initiation location. This lack of control is seen to negatively effect properties in such as wall thickness uniformity, position of key transitions associated with cone wall mass removal, ability to be delivered and overall consistency. An aspect of the invention therefore is a method of improving yield of reliable balloons formed from a tubular parison by establishing a controlled location on the parison where radial expansion is initiated.

By initiating expansion within a predetermined area of the parison, balloon product consistency can be improved within a production batch and from batch to batch. In some cases the balloons may be reliably specified to withstand higher pressure inflations, may be produced with lower wall thickness, improved distension and/or reinflation properties, or may be produced from materials currently practicable as balloon materials.

In another aspect, the invention allows for the location of initiation to be optimized for a given parison and balloon design to improve the average physical properties of the balloons produced.

In the apparatus of the invention an initiation zone, i.e. an area on the parison which is heated to a higher temperature than the adjacent parison material, is deliberately created, at least transiently during the radial expansion step. The initiation zone provides a reproducible site from which balloon expansion is initiated. In specific embodiments the initiation zone is an annular ring area.

Heating of the parison may be provided externally. In some embodiments the mold, or the mold heating system, may be modified to provide different temperatures at specific locations along the parison. An initiation-effective higher temperature is applied to a parison area designated as the desired initiation site, i.e. the initiation zone, at least transiently. In alternate embodiments the initiation zone may be heated internally while overall mold heating is applied externally, or vice-versa. Initiation zone heating may be provided internally, for instance, from a fiber-optic conveyed laser beam. Other embodiments are described in the detailed description provided herein.

DETAILED DESCRIPTION OF THE INVENTION

Figure 1:
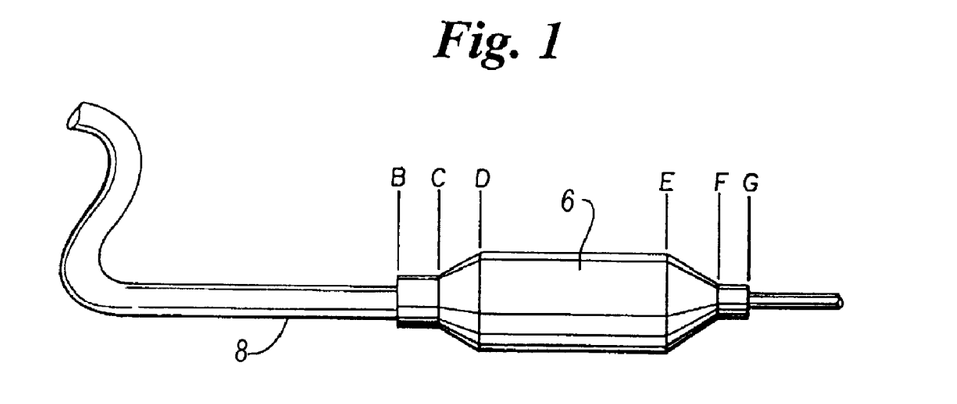
FIG. 1 is a schematic side view of a balloon catheter, the balloon prepared in accordance with the invention.

Referring to FIG. 1, a balloon 6 of the invention is shown mounted on a medical catheter 8. The balloon 6 has a proximal waist from B to C, a proximal cone from C to D, a body portion from D to E, a distal portion from E to F, and a distal waist from F to G. The proximal waist is bonded to the catheter outer shaft and the distal waist is bonded to the catheter inner. While this is a typical configuration, other configurations are possible, for instance where the body portions is stepped, or where the distal waist is bonded to the outer, and should be considered to come within the scope of the disclosure herein.

The balloon may be formed of any material which may be made by radial expansion of a tubular parison, typically thermoplastic polymers. It is possible to make balloons from a variety of thermoplastic polymers. References illustrating the materials and methods of making catheter balloons have been identified in the background section above. Such materials may include low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone). Physical blends and copolymers of such materials may also be used.

Orientable polyesters, especially polyethylene terephthalate (PET), are among the preferred materials for forming catheter balloons. Suitable PET polymers have an initial intrinsic viscosity of at least 0.5, for instance, 0.6-1.3. Other high strength polyester materials, such as poly(ethylene napthalenedicarboxylate) (PEN); and poly(butylene terephthalate may also be used. Polyester copolymers such as the random copolymer made from dimethyl terephthalate dimethyl isophthalate and ethylene glycol described in U.S. Pat. No. 5,330,428 Wang, et al. may also be employed.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The balloon may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4 butanediol chain extender. Tecothane® 1065D and 1075D are examples. Other polyurethanes which have been used are Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al, U.S. Pat. No. 6,146,356 to Wang, et al., and U.S. Pat. No. 6,572,813, to Zhang, et al.

Other suitable polymeric materials include Engage® from DuPont Dow Elastomers (an ethylene alpha-olefin polymer) and Exact®, available from Exxon Chemical, both of which are thermoplastic polymers and are believed to be polyolefin elastomers produced from metallocene catalysts. These are compliant materials which provide a balloons which have a substantial range of available diameters to which they may be expanded and still recover elastically.

Balloons of the invention may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax® trademark by Elf Atochem North America, Inc., Philadelphia Pa. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments.

It is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

Examples of thermoplastic polyimides are described in T. L. St. Clair and H. D. Burks, "Thermoplastic/Melt-Processable Polyimides," NASA Conf. Pub. #2334 (1984), pp. 337-355. A suitable thermoplastic polyimide is described in U.S. Pat. No. 5,096,848 and is available commercially under the tradename Aurum® from Mitsui Toatsu Chemicals, Inc., of Tokyo, Japan.

Examples of liquid crystal polymers include the products Vectra® from Hoechst Celanese; Rodrun® from Unitika; LX and HX series polymers and Zenite™ polymers from DuPont; Sumikosuper™ and Ekonol™ from Sumitomo Chemical; Granlar™ from Grandmont; and Xydar® from Amoco. Suitably the liquid crystal polymer materials are blended with another thermoplastic polymer such as PET, nylon 12, or a block copolymer such as Pebax® 7033 or 7233 or Arintel® EM 740 or Hytrel 8230. The liquid crystal polymer may be present as fibers in a matrix of the blend polymer.

The balloon material may be multilayered, for instance combining an outer layer of a material which is relatively soft and flexible, and/or lubricious, with an inner layer of a stronger polymer. Alternatively, or additionally, an innermost layer may be provided which is selected for compatibility with direct bonding, e.g. by fusion welding, or adhesive bonding, to the catheter material.

The balloon parison may be a straight tube, as extruded, or after extrusion and axial stretching. However, the invention has particular advantages where the tubular parison is not homogenous along its length. It may have a varying thickness, for instance resulting from parison processing such as the necking steps described in U.S. Pat. No. 4,963,313, Noddin, et al, U.S. Pat. No. 5,087,520, Wang, et al, or U.S. Pat. No. 5,087,394, Keith, or grinding steps such as described in U.S. Pat. No. 6,193,738, Tomaschko et al. The parison may have a surface pattern, for instance with longitudinal stripes or protrusions to produce a balloon with longitudinal reinforcement or which has a stent retaining surface property. The balloon mold may have a multiple-stepped diameter such as described in U.S. Pat. No. 6,290,485, Wang. The parison may be formed of segments of different material such as described in U.S. Pat. No. 6,024,752, Horn et al.

When molding polymer systems from a tubular parison, during the initial stages of the molding process, the polymer parison requires a thermally-induced initiation point, allowing the balloon to begin to blow and form in the mold in a controlled manner. The ability to control this initiation location has been demonstrated to be a key factor to successful, efficient, high-performance balloon molding. The initiation location is typically dictated by the temperature gradient location within the mold. Typically this gradient is not well controlled.

The present invention pertains to a molding system for a medical balloon which is designed to confine the polymer molding initiation point, within a specific zone, resulting in the production of more consistent, higher performance balloon components. The improved process equipment, described above, utilizes an isolated, localized, accurate, heat source. This isolated heat source could be formed by heat delivery via laser or fiber optic technology, to improve the predictability of the molding process, or zoned infrared heat transfer, resulting in improved balloon properties, consistency, and eliminating the need for fluid immersion. The balloon mold systems that are currently available do not utilize internal heat sources.

The transformation of the tubular parison into the balloon is typically performed in a mold, although sometimes a free-blowing technique is used where control of parison temperature and the applied pressure are used to directly fix the balloons size.

A typical method for blowing a balloon comprises extruding a polymeric tubular parison having a first outer diameter. The tubular parison is then radially expanded to a second outer diameter, optionally with a concurrent or intermediate axial stretching step. Radial expansion is accomplished by heating at least a portion of the tubular parison to a first elevated temperature while subjecting the interior of the tubular parison to an expansion pressure. Optionally, while still under pressure, the expanded tubular parison is heated to a second elevated temperature. Preferably, the first elevated temperature is greater than the glass transition temperature of the polymeric material forming the tubular parison.

For coronary angioplasty catheter balloons (balloon diameters of about 1.5-4.0 mm), single wall thicknesses of less than 0.001 inches, preferably less than 0.0007 inches, are conventional. Wall strengths for such balloons are in excess of 15,000, typically at least 18,000 psi, and in most cases in the range of about 20,000 to 32,000 psi. For peripheral angioplasty, balloons of up to 10 mm diameter may be used, and in such cases somewhat thicker walls may be employed. Even with a 10 mm balloon, wall thicknesses of about 0.0015 mm or less can be employed to provide balloons with burst pressures of at least 10 atm. Suitably the balloons are formed by expansion of tubing at a hoop ratio (mold diameter/tubing ID) of between 3 and 8, preferably between 4 and 7.

In one embodiment of the present invention, the method for forming the balloon comprises disposing a polymeric tubular parison within a mold. The interior of the tubular parison is then pressurized. At least a portion of the tubular parison ("effective portion"), is heated to form the tubular product into a balloon. The heating of the effective portion is controlled so that a particular selected minor region thereof ("initiation zone"), is heated, at least transiently, to a temperature higher than the remainder of the effective portion ("remainder portion"), of the parison. In this way initiation of blowing can be reproducibly produced within the initiation zone from balloon to balloon.

The increased temperature of the initiation zone may be from about 2° C. to about 100° C. higher, for instance, from about 5° C. to about 30° C. higher, or from about 7° C. to about 15° C. than the blowing temperature, i.e. the temperature to which the remainder of the effective portion is heated. The remainder portion may be heated to a temperature at which the particular material will form a balloon by pressurization in conventional manner. The blowing temperature may be at least 10° C., more preferably about 20° C. or more, and in some cases may be 40° C. or more, above the glass transition temperature of the polymeric material forming the parison. In the case of a block copolymer these temperatures are typically taken relative to the highest glass transition temperature of the material. Typically the temperature to which the remainder portion is heated is from about 80° C. to about 150° C. for most thermoplastic materials used to form medical balloons for catheters and the like.

The location, size and shape of the initiation zone may be varied as needed to satisfactory balloon properties. The shape may be for instance an annular ring. The ring is desirably not more than 2 mm in longitudinal length, preferably 1 mm or less. In some embodiments employing focused light beams initiation zones of 0.05 mm may be practicable. In at least some embodiments the location of the initiation zone will correspond to a portion of the balloon body (i.e. between opposed end cone regions of the balloon). In another embodiment the initiation zone may be a portion corresponding to a cone region of the balloon or a transition site between a cone and the balloon body.

Increased temperature may be applied to a selected initiation zone via selective differential heating of the mold surfaces, or by selective direction of energy at the parison. Selective direction of energy may be applied to inner or outer surfaces of the parison, or a combination of the two.

Figure 2:
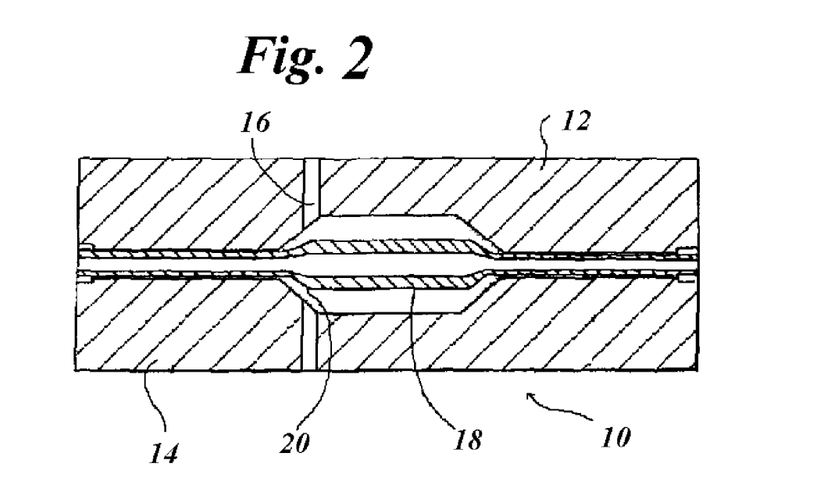
FIGS. 2-5 are schematic cross-sectional views of mold/parison assemblies constructed in accordance with various alternative embodiments of the invention.

FIG. 2 shows one embodiment of the invention. An assembly 10 comprises a mold form and parison. The mold form comprises heat conductive segments 12, 14 and a window segment 16 which is transparent to light of a wavelength or wavelength range which can induce heating of the material of the parison 18. Heat is applied to the parison 18 via mold segments 12, 14 in a conventional manner, for instance dipping, block heating or the like. For at least an initial portion of the balloon blowing time, however, light energy is directed through the window segment to an initiation zone 20 on the parison. An energy flux is applied to the initiation zone which is effective to heat the initiation zone at a faster rate or to a higher temperature than the adjacent portions of the parison so that balloon blowing is initiated within the initiation zone. The light energy applied may comprise infrared wavelengths or and/or any wavelengths outside the infrared. In at least some instances light in the visible or UV spectrum will give effective heating of the parison material. The light energy may be essentially monochromatic, as is produced by a laser light source. Broader spectrum sources such as halogen lamps, xenon flash lamps, mercury lamps, tungsten filament lamps, and the like, may also be useful in some cases, if provided with optics capable of delivering sufficient light energy via window 16 to the interior of the parison at the desired initiation zone 20. The light beam may be pulsed and the mold or light source may be moved as needed to achieve the desired level of heating in an initiation zone configured as desired. Preferably optics are employed which apply the light energy concurrently around the circumference of the parison initiation zone 20.

An alternative implementation of the assembly shown in FIG. 2 applies a heated pressurized fluid to the interior of parison 18, in the manner of U.S. Pat. No. 5,304,340, Downey, to form the balloon. The mold segments 12, 14 are not heated, but light energy is applied to the outer surface of the parison in the initiation zone through window 16, for at least an initial portion of the blowing time.

Figure 3:
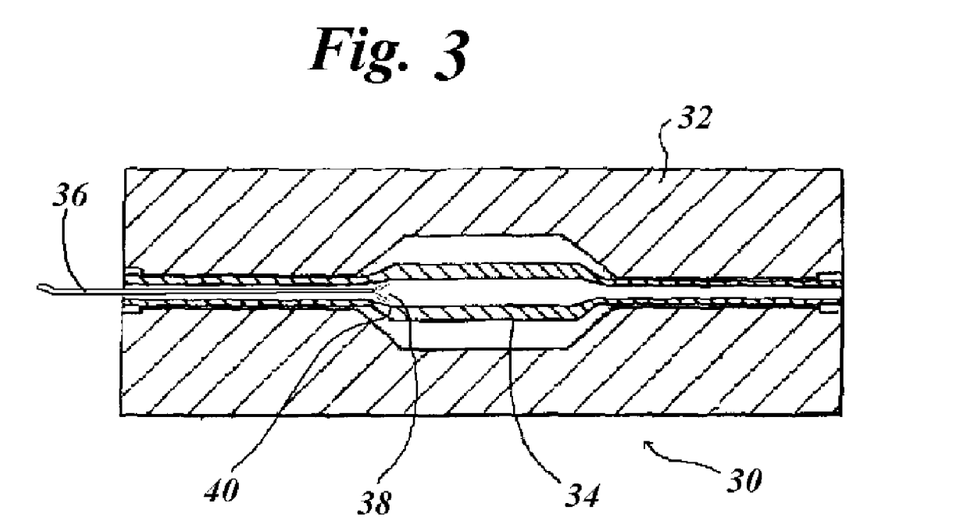

FIG. 3 illustrates another embodiment of the invention. An assembly 30 includes a mold form 32 of conventional design made of a heat conductive material and heated in a conventional manner. A parison 34 is located within the mold. An optical fiber 36 is inserted into the parison. The optical fiber carries a light beam 38, for instance a laser beam, which is directed to contact the interior surface of the parison and cause localized heating in the initiation zone 40. The parison/optical fiber assembly is then activated to form the balloon, for instance by dipping the assembly in a heated fluid and pressurizing the interior of the parison, while the light beam is activated and directed, via the optical fiber, at the inside surface of the parison initiation zone. The light beam may be pulsed and the fiber may be moved as needed to achieve the desired level of heating in an initiation zone configured as desired. Application of light energy may be timed to heat the initiation zone for a shorter duration than the mold dwell time in the heating fluid so that the balloon portion ultimately formed from the initiation zone is very similar to the adjacent portions of the balloon. Suitable optics and/or a mechanical rotation system, not shown, may optionally be employed to spin the fiber or the mold/parison assembly, on its longitudinal axis, to facilitate uniform distribution of the light energy over an annular initiation zone. The light beam 38 may be a infrared beam, however, beams of wavelengths outside the infrared, for instance in the visible or UV spectrum will give effective heating in at least some cases. Broader spectrum sources such as halogen lamps, xenon flash lamps, mercury lamps, tungsten filament lamps, and the like, may be useful in some cases if provided with optics capable of delivering sufficient light energy via fiber 36 to the interior of the parison at the desired initiation site.

As stated above, the parison/optical fiber/mold assembly of FIG. 3, in some embodiments, is dipped into heated fluid to blow the balloon. In other embodiments the parison and optical fiber are located in a mold which is heated by block heaters, or heated by fluid circulating in a sleeve surrounding the mold, to a substantially uniform temperature.

Figure 4:
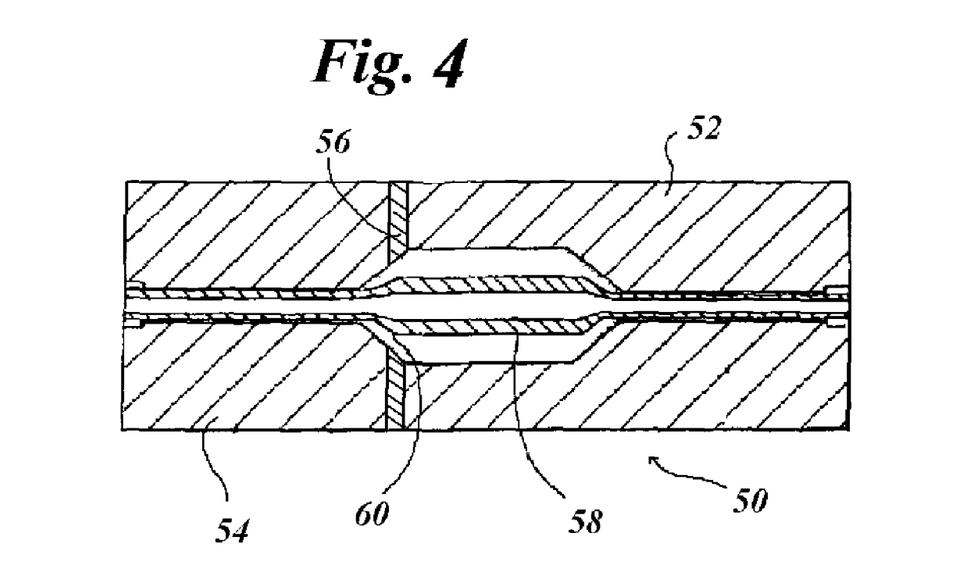

In FIG. 4, another mold form/parison assembly, 50, is shown. The mold form comprises heat conductive segments 52, 54 and 56. Segment 56 is heated to a higher temperature than segments 52 and 54, radiantly heating the parison 58 in the initiation zone 60 to a higher temperature than the adjacent portions of the initiation zone 60. Separate heaters may be associated with the mold segments 52, 54, 56 to effect the differential heating. The heaters may be, for instance, electrical resistance heaters or IR lamps. Separate controls will be associated with at least the heater or heaters associated with segment 56, relative to those associated with segments 52, 54.

As an alternative to a multi-segment mold, the mold surface may be varied to selectively radiate heat from a surface region adjacent the desired initiation zone at a greater intensity than is radiated from the remaining mold surface. Differential radiation can be produced by changing surface coating material or texture, even though the mold surfaces are all the same temperature. Selective anodization and/or polishing of mold surfaces can be used to impart differential radiating characteristics to the mold surface.

Figure 5:
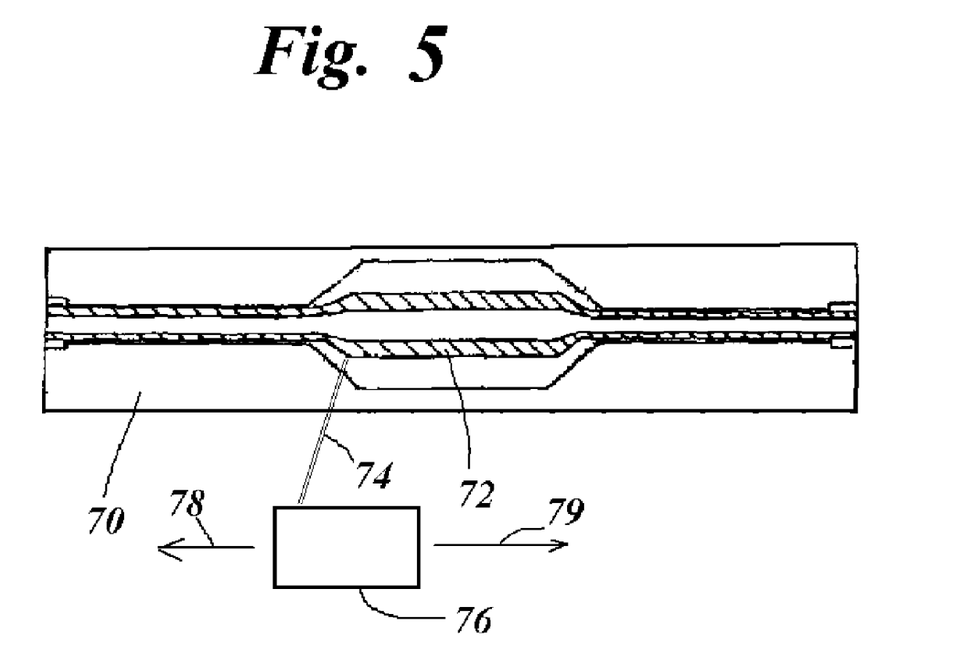

In a further variation depicted in FIG. 5, the entire mold 70 may be transparent. A focused light beam 74 is transmitted through the transparent mold to the desired initiation zone on the parison 72 from an external light source 76. The light source is movable longitudinally as indicated by arrows 78, 79. Suitably the light is applied to an annular initiation zone by rotating the mold/parison assembly under the laser beam, by rotating the beam around the mold or by an optical system that produces an annular beam directed at the desired initiation site. A high intensity infrared laser may be used with an IR transmissive mold form. Heated and pressurized inflation fluid may be used to blow the balloon or unheated inflation fluid may employed and the beam 74 directed through a heated fluid surrounding the mold 70 which is substantially transparent to the beam. The initiation zone size and location may be changed simply by adjusting a beam focus, a beam direction or relative location of the mold and the beam source.

In some cases a beam which is moved rapidly back and forth over the mold of FIG. 5 may be used as the sole heating source. A longer beam duration over the desired initiation site, or a equivalent parameter change such as a altered pulse rate or pulse interval, may be implemented to selectively heat the initiation zone of the parison to a higher temperature, for a time at least until initiation has occurred, may be used to practice the invention hereof.

In a further alternative embodiment, the tubular parison is heated as an external heater traverses along the length of the mold according to a preset program, optionally stopping for programmed intervals at specific locations. The speed of cycling from one end of the parison to the other, and back, can be controlled to keep the temperature across the mold within a particular differential. Varying the time spent at a location and/or the rate of travel can produce a blowing cycle in which initiation is controlled to occur in a specific zone of the parison. Of course, the parison may be moved relative to a stationary heater in a completely equivalent manner. A secondary heating system can be employed to control the temperature differential between the initiation zone and the remainder of the effective region of the parison. In one embodiment, the pressurized fluid used to expand the parison may be heated to provide such a secondary heating system.

In some embodiments of the invention mold heaters set to stabilize at the same temperature are turned on in a slight delay sequence between heaters for the initiation zone and those controlling the remainder to the effective region of the parison, so that at the time of initiation there is a temperature differential between the initiation zone and the remainder portion of the parison, despite the use of a common set temperature.

In a still further embodiment a totally dynamic system is employed for the blowing step such that the balloon is fully blown and cycled to a cooling or heat-set step, without the heater set temps ever having been reached. In such a system only the sequence of activating the heaters will be relevant, and so the heater set points for the initiation zone may actually be lower than the set points of the heaters for remainder portion without departing from the invention hereof.

Combinations of the techniques and systems described herein for controlling initiation of blowing may also be employed. In some embodiments of the invention, the tubular parisons may be pre-stretched axially before they are radially expanded or axially stretched concurrently with the radial expansion step.

Systems employing light energy, such as depicted in FIGS. 2, 3 and 5, have an advantage over those relying on surface radiation differentials in that optical focusing techniques are straightforward and so very narrow initiation zones can be employed.

It should be understood that the initiation zone should be optimally located for a particular balloon parison. Optimal initiation zones may be located on cone or body areas, or at transitions from waist to cone or cone to body portions. In this regard, an embodiment as depicted in FIG. 3 or FIG. 5 is highly advantageous since the fiber location, beam focal size, and beam pulse rate can all be easily varied in the same mold apparatus over wide ranges.

After initiation has been effected and the balloon has been blown to the desired configuration, the balloon may optionally be subjected to a heat-set step, which typically involves heating the formed balloon to a temperature higher than the blowing temperature, which in the case of the present invention is taken as the temperature of the effective region outside the initiation zone. Typically the heat set temperature will be from 10° C. to 50° C. higher than the blowing temperature. The second elevated temperature is sufficiently high to thermoset the polymeric material forming the tubular product. The second elevated temperature may be less, equal or greater than the first elevated temperature. Preferably, the second elevated temperature is equal to or greater than the first elevated temperature.

Also typically the heat set temperature will be substantially uniform over the balloon surface. This may be done by changing heating baths, changing fluid in a bath or sleeve heating system, programmed heating of block heaters or the like. The heat set time is typically conducted for a time which is effective to increase the degree of crystallization of the balloon material; reduce radial shrinkage; reduce axial growth; or to provide a combination of two or all three of these effects, all taken relative to the un-heat set balloon. Suitable heat set times and temperatures are known in the art.

In addition to heat setting, post-blowing processing can include a thinning of cone and/or waist regions of the balloon, for instance as shown in U.S. Pat. No. 6,287,506, Hudgins et al., or U.S. Pat. No. 5,334,146, Ozasa.

An apparatus as in FIG. 5 can also be used to selectively heat cone and waist portions of the balloon after it has been blown by directing the light beam at those locations while the balloon is still in the mold. This may be done or to reduce orientation in a cone/waist region or to selectively reduce wall thicknesses. Reduction of orientation in these regions may be desirable, for instance, to improve bonding properties, stress distribution properties or softness properties of the cone and/or waist regions. When coupled with application of axial tension, selective heating of the cone and/or waist regions can be used to reduce the cone and or waist thickness after the balloon has been blown.

Selective removal of material from a specific zone of a formed balloon, such as a cones and/or waist, or selective removal of orientation, also be achieved on a balloon which has been removed from the mold. The balloon is pressurized and the beam is directed to the sight, using an annular laser light beam, a beam which rotates around the balloon or rotation of the balloon under the beam. In the case of orientation reduction, the balloon material is heated locally by the beam until the desired loss of orientation occurs. Selective removal of material can be achieved by laser induced ablation, or by tensioning the ends of the balloon so that material from the locally heated regions is drawn out.

In any of the processes described herein involving the provision of light energy to a parison, or to a balloon substrate, the effectiveness of heating may be enhanced by incorporating light absorbing compounds into the polymeric material of the substrate or into a coating applied to the surface of the substrate. In the case of a coating, the light absorber may be selectively applied to the area designated to be selectively heated. With light absorbers selectively applied to the substrate, in some cases it may be possible to utilize such differences to obtain selective or higher temperature heating from a uniformly applied heat source. Examples of IR absorbers which may be suitable include, carbon black and titanium dioxide. Optionally, a light absorbing coating may be removed after the balloon blowing or thinning operation has been completed.

All published documents, including all U.S. patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should be also taken as alternatively written in each singly dependent claim format which creates a dependency from a antecedent-possessing claim other than the specific claim listed in such dependent claim below.

The invention claimed is:

1. A process for forming a medical device balloon which comprises the steps of
providing a tubular parison of polymeric material, and
radially expanding an effective portion of the parison by application of heat and internal pressure to form the balloon,
wherein
in the application of heat to the parison during the radially expanding step, the heating of the parison is performed over a heating time and for at least an initiation portion of the heating time a preselected initiation zone on the parison is heated to a temperature higher than the remainder of the effective portion of the parison,
the parison is radially expanded within a heated mold, and the mold is heated to a substantially uniform temperature, and a internal heating source is provided which applies additional heat to the interior of the parison at said initiation zone.

2. A process as in claim 1 wherein
the formed balloon has a pair of opposed end waist portions, a pair of end cone portions connected to the waist portions and a body portion between the end cone portions,
the effective portion of the parison has waist-forming, cone-forming and body-forming portions from which the balloon's corresponding portions are formed, and
the initiation zone is a minor portion of the parison located on the body-forming portion of the parison.

3. A process as in claim 2 wherein the initiation zone is an annular portion of the parison.

4. A process as in claim 2 wherein the initiation zone is a spot region of the parison.

5. A process as in claim 1 wherein the internal heating source comprises an optical fiber located extending into the parison from one end thereof at least during the initiation portion of the heating time, the optical fiber configured to deliver energy to said initiation zone of the parison.

6. A process as in claim 5 wherein the energy delivered is infrared, visible or UV light, or a combination thereof.

7. A process as in claim 1 wherein the internal source comprises a laser configured to direct energy to the initiation zone of the parison.

8. A process for forming a medical device balloon which comprises the steps of
providing a tubular parison of polymeric material, and
radially expanding an effective portion of the parison by application of heat and internal pressure to form the balloon,
wherein
in the application of heat to the parison during the radially expanding step, the heating of the parison is performed over a heating time and for at least an initiation portion of the heating time a preselected initiation zone on the parison is heated to a temperature higher than the remainder of the effective portion of the parison,
the parison is heated with a combination of internal and external heat sources which apply heat respectively to internal and external surfaces of the parison, and
the parison is heated substantially uniformly from an external heat source and supplemental heat is provided to the initiation zone from an internal heat source.

9. A process as in claim 1 wherein the polymeric material is selected from the group consisting of polyolefin polymers and copolymers, poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone).

10. A process for forming a medical device balloon which comprises the steps of
providing a tubular parison of polymeric material, and
radially expanding an effective portion of the parison by application of heat and internal pressure to form the balloon,
wherein
in the application of heat to the parison during the radially expanding step, the heating of the parison is performed over a heating time and for at least an initiation portion of the heating time a preselected initiation zone on the parison is heated to a temperature higher than the remainder of the effective portion of the parison, and
the polymeric material further comprises a light absorbent additive.

11. A process as in claim 1 wherein the increased temperature of the initiation zone is from about 2° C. to about 100° C. higher, than the temperature to which the remainder of the effective portion is heated.

12. A process as in claim 1 wherein the tubular parison comprises a plurality of layers of polymeric material.

13. A process for forming a medical device balloon which comprises the steps of
providing a tubular parison of polymeric material, and
radially expanding an effective portion of the parison by application of heat and internal pressure to form the balloon,
wherein
in the application of heat to the parison during the radially expanding step, the heating of the parison is performed over a heating time and for at least an initiation portion of the heating time a preselected initiation zone on the parison is heated to a temperature higher than the remainder of the effective portion of the parison, and
at least the initiation zone is coated with a coating comprising a light absorbent compound.

14. A process as in claim 10 wherein
the formed balloon has a pair of opposed end waist portions, a pair of end cone portions connected to the waist portions and a body portion between the end cone portions,
the effective portion of the parison has waist-forming, cone-forming and body-forming portions from which the balloon's corresponding portions are formed, and
the initiation zone is a minor portion of the parison located on the body-forming portion of the parison.

15. A process as in claim 14 wherein the initiation zone is an annular portion of the parison.

16. A process as in claim 14 wherein the initiation zone is a spot region of the parison.

17. A process as in claim 10 wherein the polymeric material is selected from the group consisting of polyolefin polymers and copolymers, poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone).

18. A process as in claim 10 wherein the tubular parison comprises a plurality of layers of polymeric material.

19. A process as in claim 13 wherein
the formed balloon has a pair of opposed end waist portions, a pair of end cone portions connected to the waist portions and a body portion between the end cone portions,
the effective portion of the parison has waist-forming, cone-forming and body-forming portions from which the balloon's corresponding portions are formed, and
the initiation zone is a minor portion of the parison located on the body-forming portion of the parison.

20. A process as in claim 19 wherein the initiation zone is an annular portion of the parison.

21. A process as in claim 19 wherein the initiation zone is a spot region of the parison.

22. A process as in claim 13 wherein the polymeric material is selected from the group consisting of polyolefin polymers and copolymers, poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone).

23. A process as in claim 13 wherein the tubular parison comprises a plurality of layers of polymeric material.

* * * * *